United States Patent [19]

Armitage et al.

[11] 4,036,989
[45] July 19, 1977

[54] ANTI-INFLAMMATORY COMPOSITION AND METHOD CONTAINING 2-FLUORO-4-ISOPROPYLBIPHENYL

[75] Inventors: Bernard J. Armitage; John S. Nicholson, both of Beeston, England

[73] Assignee: The Boots Company Limited, England

[21] Appl. No.: 473,485

[22] Filed: May 28, 1974

[30] Foreign Application Priority Data

June 1, 1973 United Kingdom ............ 26276/73

[51] Int. Cl.² .................... A61K 31/03; C07C 43/20
[52] U.S. Cl. ............................. 424/353; 260/612 R; 260/649 F; 260/649 R; 424/14; 424/340; 424/341
[58] Field of Search .................. 424/340, 341, 353

[56] References Cited

U.S. PATENT DOCUMENTS

| | | | |
|---|---|---|---|
| 3,649,679 | 3/1972 | Marshall | 424/340 |
| 3,745,223 | 7/1973 | Marshall | 424/203 |

OTHER PUBLICATIONS

Smith, et al., Chem. Abs., 1960, vol. 54, pp. 13083, 13084.

*Primary Examiner*—Dale R. Ore
*Attorney, Agent, or Firm*—Gordon W. Hueschen

[57] ABSTRACT

Novel substituted aromatic hydrocarbons and ethers, and pharmaceutical compositions containing them, are described. They have pharmaceutical activity, e.g. as anti-inflammatory agents.

5 Claims, No Drawings

ANTI-INFLAMMATORY COMPOSITION AND METHOD CONTAINING 2-FLUORO-4-ISOPROPYLBIPHENYL

This invention relates to novel hydrocarbons and ethers and in particular to hydrocarbons and ethers having valuable therapeutic properties.

According to the invention there is provided a compound of formula I

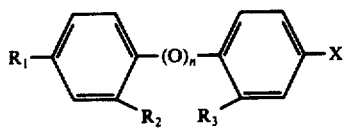

in which $n = 0$ or 1; X is an alkyl or alkenyl group of 2 to 6 carbon atoms, and $R_1$, $R_2$ and $R_3$ may be the same or different and are hydrogen, chlorine or fluorine, and when $n$ is 0 may also be lower alkyl, lower alkoxy, hydroxy or bromine; with the proviso that at least one of $R_1$, $R_2$ and $R_3$ is not hydrogen and when $n$ is 0 at least one of $R_2$ and $R_3$ is not hydrogen.

The compounds of the invention have valuable therapeutic properties including anti-inflammatory, analgesic and antipyretic activity.

X is preferably isopropyl, but other suitable groups include ethyl, n-propyl, n-butyl, 1-methylpropyl, 1-methylbutyl and isopropenyl.

The most preferred compounds are those in which $n$ is 0. When $R_1$, $R_2$ and $R_3$ are substituents these are preferably chlorine or fluorine, the latter being particularly preferred. When $R_1$, $R_2$ or $R_3$ is lower alkyl this is generally methyl or ethyl and when lower alkoxy, generally methoxy.

The particularly preferred compounds are those in which $n$ is 0. Examples of particularly valuable compounds are the following

| n | R1 | R$_2$ | R$_3$ |
|---|----|----|----|
| 0 | H | F | H |
| 0 | H | H | F |
| 0 | H | F | F |
| 0 | F | F | H |
| 0 | F | H | F |
| 0 | F | F | F |
| 1 | F | H | H |
| 1 | F | F | H |
| 1 | H | F | H |
| 1 | F | Cl | H |
| 1 | Cl | H | H |
| 0 | H | Cl | H |
| 0 | H | H | Cl |
| 0 | Cl | F | F |
| 0 | F | F | Cl |
| 0 | F | Cl | F |
| 0 | H | H | Br |
| 0 | H | H | Me |
| 0 | H | H | OMe |
| 0 | H | OH | H |
| 0 | OH | H | H |

The therapeutic activity of the compounds is assessed or shown in various ways. For example the anti-inflammatory activity is determined in the test described by Adams and Cobb, *Nature* 1958, 181, 733. The activity of the test compounds is compared with that of aspirin against ultraviolet light induced erythema on the depilated skin of guinea pigs.

Another way of determining anti-inflammatory activity is by the rat adjuvant arthritis test in which an arthritis is produced by injecting intradermally into the tail 0.1 ml. of a suspension of killed human tubercle bacilli (6 mg/ml) in liquid paraffin BP. A polyarthritis develops over the next 3 weeks in untreated controls. The compounds under test (vehicle only for control animals) are given daily by mouth from the day the adjuvant is injected for 21 days. On day 21 the degree of arthritis is assessed on each hind foot. The degree of inhibition produced by a compound is estimated by comparison of the total arthritic scores with those found in the controls.

This test is particularly useful in assessing the activity of compounds having a long duration of activity. Such compounds may not always have a high level of activity in acute tests such as the ultra violet induced erythema test above. However, some compounds which are not long acting may also be shown to be potent in this test.

The analgesic activity of the compounds is shown in the rat using a modification of the technique described by Randall and Selitto, *Arch. int. Pharmacodyn*, 1957, 111, 409. In this technique the analgesic effect of the drugs is compared with aspirin by determining the increase in pain threshold when pressure is applied to the inflamed foot.

The anti-pyretic effect is shown in rats in which the body temperature has been raised by a subcutaneous injection of a yeast suspension. Comparison of the compounds under test is made with graded doses of aspirin.

Methods of treating inflammatory conditions according to the invention comprise administering to the living animal body, for example, a human patient, one of the compounds of the invention in a pharmaceutically acceptable and effective dosage, administration preferably being oral. Methods of the invention also comprise the treatment of conditions of pain or pyretic conditions individually or in combination or in any combination with the inflammatory conditions by similar administration of a compound of the invention. The compounds may be administered in conventional manner for other anti-inflammatory agents, for example orally, rectally, topically or parenterally, preferably oral or rectally.

The optimum dosage rate varies with the route of administration, but normally lies within the range 0.014–14.0 mg./kg./day, more usually between 0.035–7.0 mg./kg./day. The unit dose may vary from 0.5 mg. to 1000 mg. for oral administration the dosage rate is preferably 0.5–2000 mg. per subject per day.

For ease of administration the compounds are preferably formulated as therapeutic compositions which comprise a compound of the invention in association with pharmaceutical excipients for the production of compositions for oral, rectal, topical or parenteral administration. These compositions preferably contain 0.1–90% by weight of a compound of the invention.

Preferred compositions of the invention are compositions for oral administration, and these are the conventional pharmaceutical forms for such administration. Since the compounds are generally liquids the preferred oral forms are capsules, syrups and aqueous and oily suspensions. The excipients used in the preparation of these compositions are the excipients of the pharmacist's art.

In the preparation of capsules, soft gelatin capsules may be used containing the active ingredient alone or admixed with a diluent. The liquid compositions may comprise as excipients water and sucrose to provide syrups, water, dispersing agents and suspending agents, e.g. sodium carboxymethylcellulose to provide aqueous suspensions, and a non-toxic oil, e.g. a vegetable oil such as arachis oil and a suspending agent to provide oily suspensions.

Other preferred compositions of the invention are compositions for rectal administration and these are the conventional pharmaceutical forms for such administration, such as for example suppositories with fatty glyceride or polyethylene glycol bases.

Compositions for topical use are the conventional pharmaceutical forms for such application, such as ointments, creams and lotions. Ointments and creams may be water miscible or water-immiscible in character and include emulsions prepared from emulsifying waxes and oils and those prepared from water miscible polyethylene glycols. Lotions may comprise a solution in an aliphatic alcohol with 1–4 carbon atoms which may contain a small proportion of water.

Compositions for parenteral administration are the conventional pharmaceutical forms for such administration.

The products of the present invention may of course be employed in combination with other active anti-inflammatory agents, analgesics, and antipyretic agents, or with other drugs.

The compounds of the invention have other valuable properties. For example, they possess fibrinolytic and thrombolytic activity and also inhibit platelet aggregation induced by various agents such as adrenaline.

The fibrinolytic activity is assessed by the euglobulin lysistime test described by Van Kaulla in Chemistry of Thrombolysis: Human Fibrinolytic Enzyme, 1963, p79, published by Charles C. Thomas, Springfield, Ill.

The thrombolytic activity is assessed by the hanging clot test described by Van Kaulla, J. Med. Chem. 1965, 8, 164.

The effect on platelet aggregation is assessed by the test of Born; *Nature*, 1962, 194, 927.

Drugs possessing such properties are useful in the treatment and/or prophylaxis of various thrombotic disorders. When being used in such treatment or prophylaxis they may be formulated and administered in a manner similar to that when being used as anti-inflammatory agents, as described previously.

The compounds of the invention may be made by a wide variety of methods, listed below. As the methods are, in themselves, either already known or readily apparent to those skilled in the art for making similar compounds the descriptions have been kept brief. Where the starting materials for the methods are not already known compounds, methods for their preparation will be apparent to those skilled in the art. In the following description the symbol $R_o$ is used to represent

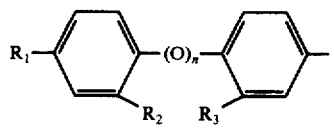

wherein $R_1$, $R_2$ and $R_3$ have the same meanings as hereinbefore.

Preparation of compounds in which X is alkyl

1. By reduction of a compound $R_oY$ in which Y is a group which can be reduced, hydrogenolysed or dehydrated and reduced to an alkyl group, e.g. a keto, hydroxy or halogen containing group or an alkenyl group.

Typical reactions include the following:

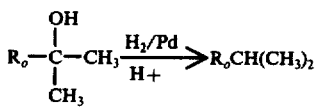

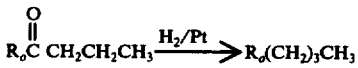

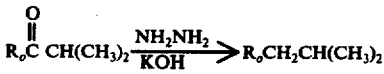

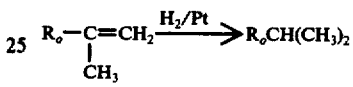

The ketones themselves may be prepared by conventional means, for example, those in which $R_3$ is hydrogen may be obtained by the Friedel Crafts reaction

(R = an alkyl group).

The hydroxy containing compounds, usually tertiary alcohols, may be prepared by conventional means,

(R = an alkyl group)

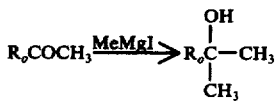

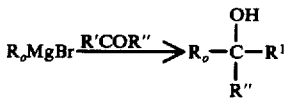

The compounds in which Y is an alkenyl group may be obtained by the methods described below for preparation of compounds in which X is alkenyl.

Preparation of compounds in which X is alkenyl

1. By dehydration of $R_oY$ in which Y is a hydroxyalkyl group e.g.

-continued

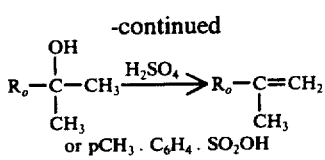

The hydroxy-containing compound may be prepared as previously described, but need not be isolated before dehydration.

2. By the Wittig reaction in which a ketone or aldehyde is reacted with a triphenylphosphinealkene

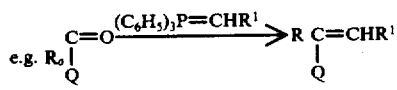

in which Q is hydrogen or alkyl and $R^1$ is alkyl.

Preparation of compounds in which X is either alkyl or alkenyl

1. By the Wurtz-Fittig reaction

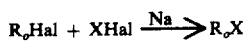

Preferably the halogen is iodine

2. By the Friedel Crafts reaction

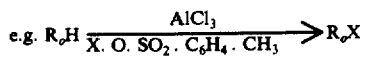

$(R_3 = H)$

3. By the Grignard reaction

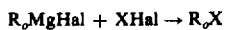

Preferably the halogen is bromine or iodine.

4. By the Ullmann reaction

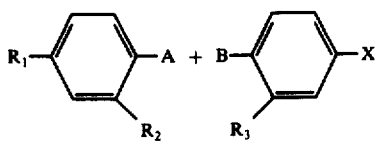

wherein at least one of A and B is halogen, e.g. bromine or iodine, and the other is hydroxy or halogen. When one of A and B is hydroxy it is preferred that it is B. This reaction is normally carried out by heating the reactants together at 100° to 350° C in the presence of a metal catalyst, e.g. copper powder. When one of A and B is hydroxy, the hydroxy compound is preferably reacted as an alkali metal derivative.

5. By reaction of a compound of formula

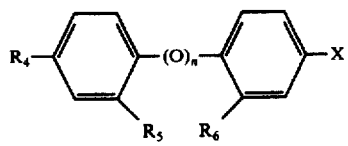

in which at least one of $R_4$, $R_5$ and $R_6$ is a group convertible to $R_1$, $R_2$ or $R_3$ the other symbols correspond to the desired values of $R_1$, $R_2$ or $R_3$ to convert the group to the desired value. Examples of such groups include amino groups which may, for example, be converted to a halogen atom in known manner. Examples of known procedures include the Sandmeyer reaction, wherein the amino compound is diazotised and reacted with a cuprous halide, and the Schiemann reaction wherein the amino compound is diazotised in the presence of a fluorinating agent to form a fluorodiazonium derivative which is then decomposed by heating to give the corresponding fluoro compound. Suitable fluorinating agents include hydrogen fluoride, fluoboric acid, fluosilicic acid and hexafluorophosphoric acid. Alternatively the amino group may be removed in known manner, so that the group becomes hydrogen.

Other examples of groups convertible to desired groups include phenolic protecting groups e.g. alkoxy, especially methoxy, benzyloxy and tetrahydropyranyloxy. These may be converted to hydroxy in known manner, e.g. by treatment with acid.

The invention is illustrated in the following examples, in which "parts" and "percentages" are by weight.

EXAMPLE 1

A solution of 4-acetyl-2-methylbiphenyl (12.8g, 0.061 mole) in dry ether (340ml) was added over 30 minutes to methyl magnesium iodide, (from magnesium, 1.8g, methyl iodide, 5.1ml, and ether 61 ml). The mixture was stirred under reflux for 5 hours, stirred overnight at room temperature and finally decomposed by the dropwise addition of hydrochloric acid (2N; 170ml). The product was isolated in ether washed with aqueous sodium thiosulphate and water, dried, evaporated, and distilled. The product solidified on standing and was recrystallized from light petroleum (b.p. 40°–60° C) to give 4-(1-hydroxy-1-methylethyl)-2-methylbiphenyl, m.p. 60°–64° C. A solution of this (5g) in ethyl acetate (50ml) containing concentrated sulphuric acid (3 drops) was hydrogenated over palladium-charcoal (10%, 0.5g) for 8 hours. The mixture was filtered and the filtrate was concentrated by evaporation. The residue was dissolved in ether (50ml), washed with aqueous sodium hydrogen carbonate, dried, evaporated and distilled to give 4-isopropyl-2-methylbiphenyl, b.p. 93°–94° C/0.3mm.

In a similar manner other tertiary alcohols were formed and then reduced to give the corresponding isopropyl derivative. The details are given in Table I.

TABLE I

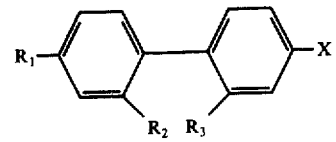

| Ex. No. | R1 | R2 | R3 | X = —CO(OH)Me₂ m.p.(° C) | X = Isopropyl b.p.(° C/mm) |
|---|---|---|---|---|---|
| 2 | H | H | F | 50–54 | 94–95/0.15 |
| 3 | F | F | F | 49–50 | 95–96/0.7 |

EXAMPLES 4–13

The procedure of Example 1 was followed except that the product from the Grignard reaction was distilled from a trace of toluene p-sulphonic acid whereby the isopropenyl compound was obtained instead of the tertiary alcohol. The compounds obtained are given in Table II.

TABLE II

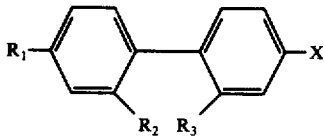

| Ex. No. | R₁ | R₂ | R₃ | X = isopropenyl b.p.(° C/mm) m.p.(° C) | | X = isopropyl b.p.(° C/mm) |
|---|---|---|---|---|---|---|
| 4 | H | H | MeO | 130–132/0.6 | | 103–105/0.15 |
| 5 | F | F | H | | 40–41 | 91–92/0.4 |
| 6 | H | F | H | | 57–58 | 124–126/3.0 |
| 7 | F | F | Cl | 140–142/2.5 | 28–29 | 90–92/0.1 |
| 8 | F | H | F | | 52–54 | 108–110/1.0 |
| 9 | H | H | Cl | | 34–35 | 108–110/0.4 |
| 10 | F | F | F | | 40–41 | 95–96/0.7 |
| 11 | H | H | F | | 32–33 | 94–95/0.15 |
| 12 | H | F | F | | 63–64 | 96–97/0.6 |
| 13 | H | H | Br | | 38–40 | 134–136/1.0 |

EXAMPLES 14–16

The procedure of Example 11 was followed but replacing the methyl magnesium iodide with in turn ethyl magnesium iodide, n-propyl magnesium iodide and n-butyl magnesium iodide. The compounds obtained are set out in Table III.

TABLE III

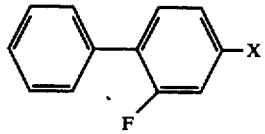

| Ex. No. | X | m.p.(° C) | b.p. (° C/mm) | X | b.p. (° C/mm) |
|---|---|---|---|---|---|
| 14 | 1-methyl-1-propenyl | 65–68 | | s-butyl | 116–117/1.0 |
| 15 | 1-methyl-1-butenyl | | 145–150/1.5 | 1-methyl-butyl | 141–143/2.0 |
| 16 | 1-methyl-1-pentenyl | | 135–140/0.4 | 1-methyl-pentyl | 133–137/0.7 |

EXAMPLE 17

Following the procedure of Example 14 there was obtained 2'-fluoro-4-(1-methyl-1-propenyl)biphenyl, m.p. 83°–85° C, which was reduced to 2'-fluoro-4-s-butylbiphenyl, b.p. 136–137/3.0mm.

EXAMPLES 18–25

A mixture of o-fluoroiodobenzene (44.4g, 0.2 mole), 4-isopropylphenol (27.2g, 0.2 mole), copper lining powder (1.0g) and potassium hydroxide (11.2g, 0.2 mole, fused with 2 ml H₂O at 180° C) was stirred at 140°–150° C for 3 hours. The cooled mass was extracted with boiling petroleum (b.p. 62°–68° C), the resulting extracts were washed with dilute aqueous sodium hydroxide, water, dried, and then concentrated by evaporation. The product was distilled to give 2'-fluoro-4-isopropyldiphenyl ether, b.p. 106°–108° C/0.5mm.

In a similar manner starting from the appropriate iodobenzene and alkylphenol the compounds set out in Table IV were obtained.

TABLE IV

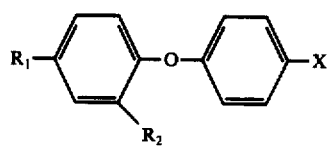

| Ex. No. | R1 | R2 | X | b.p.(° C/mm) |
|---|---|---|---|---|
| 19 | F | F | Pri | 102–104/0.5 |
| 20 | H | F | Et | 90–91/0.2 |
| 21 | H | F | Bui | 130–132/1.7 |
| 22 | H | Cl | Pri | 130–132/0.7 |
| 23 | F | F | Prn | 100/0.3 |
| 24 | F | F | But | 100–106/0.3 |
| 25 | Cl | H | Pri | 144–146/1.8 |

EXAMPLE 26

In a similar manner to the procedure of Example 18, 1-ethyl-4-iodobenzene and o-cresol were reacted to give 4-ethyl-2'-methyldiphenyl ether, b.p. 92°–94° C/0.3mm.

EXAMPLE 27

Copper lining powder (75g) was added portionwise over 30 minutes to a stirred mixture of 1-ethyl-4-iodobenzene (34.8g, 0.15 mole) and 2-bromo-1-nitrobenzene (30.3g, 0.15 mole) in nitrobenzene (250 ml) at 160°. After stirring for a further 3 hours at 160° C the solution was cooled, diluted with methylene chloride and filtered. Methylene chloride was distilled, nitrobenzene was steam-distilled, and the product was isolated in ether, and distilled to give 4-ethyl-2-nitrobiphenyl, b.p. 120°–130° C/0.1mm.

A solution of this product (18.2g) in industrial methylated spirits (45ml) was added slowly to a stirred mixture of iron powder (reduced, 17.5g), industrial methylated spirits (80ml), concentrated hydrochloric acid (1ml) and water (25ml), maintained under reflux. The mixture was heated under reflux for a further 3 hours. The mixture was then filtered and the solvent removed. in vacuo. The residue was distilled to give 2'-amino-4-ethylbiphenyl b.p. 130°–135°/1.0mm. This (14g) was mixed with tetrahydrofuran (13ml) and aqueous fluoroboric acid (80ml) and diazotised at 0°–5° C, by treatment with sodium nitrite (5.5g) in water (10 ml).

The diazonium fluoborate was collected, washed successively with dilute aqueous fluoroboric acid (10%), a mixture of ether and methanol (9:1), and ether. It was then dried and decomposed by heating under reflux with xylene (160ml). The solution was washed with dilute aqueous sodium hydroxide and water, dried, evaporated and distilled to give 4-ethyl-2-fluorobiphenyl b.p. 114°–116°/2.0mm.

EXAMPLE 28

2-Amino-4-bromobiphenyl was converted by the procedure described in Example 27, to 4-bromo-2-fluorobiphenyl, b.p. 106°–109° C/0.6mm, m.p. 38°–39° C. A solution of this (15.1g) in ether (100ml) was added slowly to a stirred mixture of magnesium (1.44g., 0.06g. atom) in ether (50ml) at a rate sufficient to maintain a steady reflux. After stirring under reflux for 1 hour, a solution of diethyl ketone (5.2g, 6.3ml, 0.06 mole) in ether (50ml) was added and reflux was continued for 2 hours. After stirring at room temperature overnight, the complex was decomposed by the dropwise addition of hydrochloric acid (2N; 150ml) and the organic layer separated, dried and evaporated. Distillation of the residue from a catalytic amount of toluene-p-sulphonic acid gave the crude product b.p. 145°–150°/2.0mm.

This was purified by chromatography on alumina to give 4-(1-ethyl-1-propenyl)-2-fluorobiphenyl, b.p. 126°–128° C/0.6mm.

This was then hydrogenated using the procedure of Example 1 to give 4-(1-ethylpropyl)-2-fluorobiphenyl, b.p. 113°–114° C/0.4mm.

EXAMPLE 29

A mixture of 4-isopropyl-2-methoxybiphenyl (3.8g from Example 5) in aqueous hydrobromic acid (150ml; 48%) and acetic acid (glacial, 50ml) was stirred under reflux for 7 hours. The mixture was cooled, diluted with water and extracted with ether. The extract was washed with water, dried, evaporated and distilled to give 2-hydroxy-4-isopropylbiphenyl, b.p. 112°–113°/0.2 mm.

EXAMPLE 30

2-Fluoro-4-isopropylbiphenyl, mixed with arachis oil, is encapsulated in soft gelatin in conventional manner to give capsules each containing 20 mg of active ingredient.

EXAMPLE 31

Suppositories weighing 1g and containing 20mg of 2-fluoro-4-isopropylbiphenyl are prepared in conventional manner using a polyethylene glycol base.

Compositions similar to those of Examples 30 and 31 are formed from the alkyl and alkenyl products of Examples 1 and 3 to 29.

We claim:

1. A therapeutic composition useful in the treatment of inflammation comprising an effective anti-inflammatory amount of the compound 2-fluoro-4-isopropylbiphenyl in admixture with a pharmaceutically-acceptable excipient.

2. The therapeutic composition of claim 1 in unit dosage form adapted for therapeutic administration wherein 0.5 to 1000 mg. of active ingredient is present per unit.

3. A method of treating inflammation in a patient which comprises administering to a patient in need of such treatment parenterally, topically, orally, or rectally an effective anti-inflammatory amount of the compound 2-fluoro-4-isopropylbiphenyl.

4. The method according to claim 3 which comprises administering 0.5 to 2000mg of the compound per kg of body weight of the patient per day.

5. The compound 2-fluoro-4-isopropylbiphenyl.

* * * * *